(12) United States Patent
Uematsu et al.

(10) Patent No.: US 11,820,733 B2
(45) Date of Patent: Nov. 21, 2023

(54) PROCESS FOR PRODUCING SULFONIC ACID GROUP-CONTAINING MONOMER

(71) Applicant: ASAHI KASEI KABUSHIKI KAISHA, Tokyo (JP)

(72) Inventors: Nobuyuki Uematsu, Tokyo (JP); Yasuhiro Nagato, Tokyo (JP); Kaishi Hori, Tokyo (JP); Kenichi Yakigaya, Tokyo (JP)

(73) Assignee: ASAHI KASEI KABUSHIKI KAISHA, Tokyo (JP)

( * ) Notice: Subject to any disclaimer, the term of this patent is extended or adjusted under 35 U.S.C. 154(b) by 688 days.

(21) Appl. No.: 16/959,432

(22) PCT Filed: Feb. 13, 2019

(86) PCT No.: PCT/JP2019/005093
§ 371 (c)(1),
(2) Date: Jul. 1, 2020

(87) PCT Pub. No.: WO2019/176425
PCT Pub. Date: Sep. 19, 2019

(65) Prior Publication Data
US 2020/0399210 A1 Dec. 24, 2020

(30) Foreign Application Priority Data

Mar. 14, 2018 (JP) ................................ 2018-046930

(51) Int. Cl.
| | | |
|---|---|---|
| C07C 303/32 | (2006.01) | |
| C07D 327/04 | (2006.01) | |
| C07F 7/12 | (2006.01) | |
| C08F 14/26 | (2006.01) | |
| C07C 309/06 | (2006.01) | |

(52) U.S. Cl.
CPC .......... *C07C 303/32* (2013.01); *C07D 327/04* (2013.01); *C07F 7/12* (2013.01); *C08F 14/26* (2013.01); *C07C 309/06* (2013.01)

(58) Field of Classification Search
CPC ... C07C 303/32; C07C 309/06; C07C 309/11; C07C 309/10; C07D 327/04; C07F 7/12; C08F 14/26; Y02E 60/50
USPC ....................................................... 528/401
See application file for complete search history.

(56) References Cited

U.S. PATENT DOCUMENTS

| | | | |
|---|---|---|---|
| 3,560,568 A | 2/1971 | Resnick | |
| 4,358,412 A | 11/1982 | Ezzell et al. | |
| 6,274,677 B1 | 8/2001 | Tatemoto | |
| 11,649,205 B2 * | 5/2023 | Uematsu | C07C 309/10 |
| | | | 562/110 |
| 2005/0075394 A1 | 4/2005 | Box et al. | |
| 2007/0088142 A1 | 4/2007 | Masanori et al. | |
| 2009/0143613 A1 | 6/2009 | Masakazu et al. | |
| 2016/0248121 A1 * | 8/2016 | Uematsu | H01M 4/505 |
| 2018/0273663 A1 * | 9/2018 | Dahlke | H01M 8/1039 |
| 2021/0074919 A1 * | 3/2021 | Fujiyoshi | H10K 71/00 |

FOREIGN PATENT DOCUMENTS

| | | | |
|---|---|---|---|
| CN | 1251576 A | 4/2000 | |
| CN | 1500075 A | 5/2004 | |
| CN | 108137750 A | 6/2018 | |
| JP | S472083 B | 1/1972 | |
| JP | S5212129 A | 1/1977 | |
| JP | S5728024 A | 2/1982 | |
| JP | 2004010562 A | 1/2004 | |
| JP | 2004018423 A | 1/2004 | |
| JP | 2004182629 A | 7/2004 | |
| JP | 2005511508 A | 4/2005 | |
| JP | 2022073879 | * 5/2022 | ........... C07C 303/44 |
| RU | 2379286 C2 | 1/2010 | |
| RU | 2503659 C1 | 1/2014 | |
| WO | 9843952 A1 | 10/1998 | |
| WO | 2017053563 A1 | 3/2017 | |

OTHER PUBLICATIONS

Mar. 12, 2021, the Supplementary European Search Report issued by the European Patent Office in the corresponding European Patent Application No. 19768637.1.
Introduction to Fluorine Chemistry 2010: The Frontiers of Basics and Applications, Apr. 2010, pp. 353-355, Fluorine Chemistry 155th Commission et al., with a partial English translation.
Mar. 26, 2019, International Search Report issued in the International Patent Application No. PCT/JP2019/005093.
Oliver Gronwald et al., Synthesis of difluoroethyl perfluorosulfonate monomer and its application, Journal of Fluorine Chemistry, 2008, pp. 535-540, vol. 129, Issue 6.
Sep. 15, 2020, International Preliminary Report on Patentability issued in the International Patent Application No. PCT/JP2019/005093.

\* cited by examiner

*Primary Examiner* — Douglas J McGinty
(74) *Attorney, Agent, or Firm* — KENJA IP LAW PC

(57) ABSTRACT

The present disclosure is directed to provide a process capable of producing a sulfonic acid group-containing monomer in a good yield, which can be used as a raw material of fluorine-based polymer electrolytes, such as membranes for fuel cells, catalyst binder polymers for fuel cells, and membranes for chlor-alkali electrolysis. A process for producing a sulfonic acid group-containing monomer represented by the general formula (3) includes the step of mixing and stirring a cyclic compound represented by the general formula (1) and a silanol compound represented by the general formula (2).

7 Claims, No Drawings

PROCESS FOR PRODUCING SULFONIC ACID GROUP-CONTAINING MONOMER

TECHNICAL FIELD

The present disclosure relates to a process for producing a sulfonic acid group-containing monomer. More particularly, the present disclosure relates to a process for producing a sulfonic acid group-containing monomer in a good yield, which can be used as a raw material of various fluorine-based polymer electrolytes, such as membranes for fuel cells, catalyst binder polymers for fuel cells, and membranes for chlor-alkali electrolysis.

BACKGROUND

Perfluoropolymers represented by the following general formula (6) have been typically used as main components of membranes for fuel cells, membranes for chlor-alkali electrolysis, and the like:

[Chemical Formula 1]

(6)

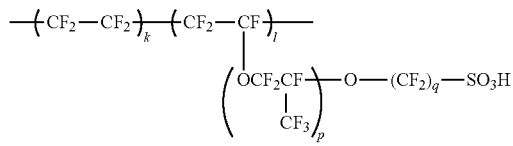

(wherein p is an integer from 0 to 6, and q is an integer from 1 to 6).

It is well known that a polymer represented by the general formula (6) can be produced by subjecting a copolymer of a fluorinated monomer represented by the following general formula (7) and tetrafluoroethylene (TFE) to saponification and acid treatment:

[Chemical Formula 2]

(7)

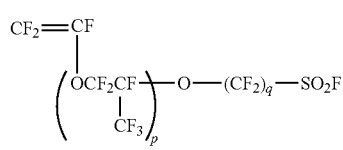

(wherein p and q are as defined in the general formula (6)).

Among fluorinated monomers represented by the general formula (7), polymers produced from monomers where p is 1 and q is 2-4 have been widely used. It is well known that monomers where p is 1 and q is 2-4 can be produced via the following route:

[Chemical Formula 3]

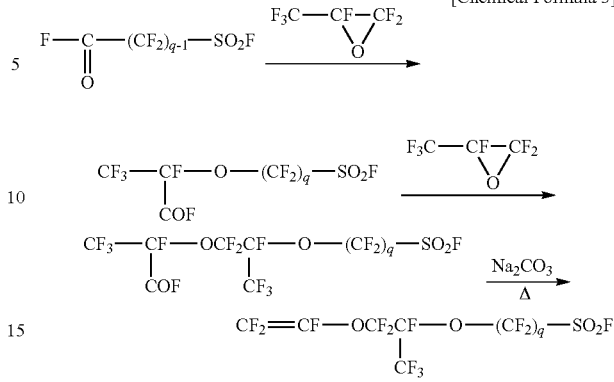

In the meantime, it is well known that polymers where p is 0 in the general formula (6) have shorter spacer portions between the main chain and sulfonic acid groups than those in polymers where p is 1 or more, and thus have higher glass transition temperatures and higher strengths than polymers where p is 1 or more.

Fluorinated monomers represented by the general formula (7) where p is 0, which are raw materials of polymers where p is 0, have the shortcoming of difficulty in synthesis. More specifically, it is well known that, when $CF_3CF(COF)O(CF_2)_qSO_2F$ is subjected to decarboxylation and vinylation in the same manner as fluorinated monomers represented by the general formula (7) where p is 1, the cyclization reaction becomes dominant and the yield of the fluorinated monomer represented by the above general formula (7) having the short chain structure where p is 0 becomes extremely low. For example, when q is 2, only cyclization proceeds, making production of the fluorinated monomer difficult (see NPL 1, for example).

[Chemical Formula 4]

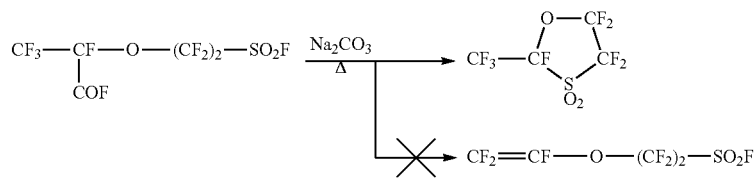

As another process for synthesizing a fluorinated monomer represented by the general formula (7) where p is 0, a synthesis process using a chlorine atom-containing fluoroepoxide is disclosed (see PTL 1, for example). This process, however, is far from practical because it needs a special chlorine atom-containing fluoroepoxide which is not widely available and synthesis of which is cumbersome.

As a process for synthesizing a fluorinated monomer represented by the general formula (7) where p is 0, PTL 2 discloses a production of a sulfonic acid group-containing monomer ($CF_2{=}CFO(CF_2)_2SO_3Na$). In this process, a 5-membered cyclic compound is produced through decarboxylation of $CF_3CF(COF)O(CF_2)_2SO_2F$ by heating with sodium carbonate, and the 5-membered cyclic compound is then subjected to a reaction with sodium methoxide ($NaOCH_3$), so that the resultant sulfonic acid group-containing monomer is available for copolymerization with TFE. Further, it also discloses a process for producing a fluorinated monomer represented by the general formula (7) where p is 0 and q is 2 ($CF_2=CFO(CF_2)_2SO_2F$) by subjecting this sulfonic acid group-containing monomer to a reaction with phosphorus pentachloride to produce $CF_2=CFO(CF_2)_2SO_2Cl$, which is then subjected to a reaction with sodium fluoride.

[Chemical Formula 5]

$CF_3-CF-O-(CF_2)_2-SO_2F$ $\xrightarrow{Na_2CO_3, \Delta}$
|
COF $CF_3-CF\overset{O-CF_2}{\underset{S}{\underset{O_2}{<}}}CF_2$ $\xrightarrow{NaOCH_3}$ $CF_2=CF-O-(CF_2)_2-SO_3Na$ $\xrightarrow{PCl_5}$
$CF_2=CF-O-(CF_2)_2-SO_2Cl$ $\xrightarrow{NaF}$
$CF_2=CF-O-(CF_2)_2-SO_2F$

CITATION LIST

Patent Literature

PTL 1: JP S57-28024 A
PTL 2: U.S. Pat. No. 3,560,568 A
PTL 3: WO 98/43952 A

Non-Patent Literature

NPL 1: The 155th Committee on Fluorine Chemistry, Japan Society for the Promotion of Science, "Introduction to Fluorine Chemistry 2010: The Frontiers of Basics and Applications," April 2010, pp. 353-355.
NPL 2: Gronwald, Oliver, et al. "Synthesis of difluoroethyl perfluorosulfonate monomer and its application." Journal of Fluorine Chemistry 129 (2008) 535-540.

SUMMARY

Technical Problem

In an actual process, though, when the 5-membered cyclic compound, which is produced through decarboxylation of $CF_3CF(COF)O(CF_2)_2SO_2F$ by heating with sodium carbonate, is subjected to a reaction with sodium methoxide, a complex reaction mixture is produced in which the amount of production of the target sulfonic acid group-containing monomer ($CF_2=CFO(CF_2)_2SO_3Na$) is small, but compounds presumably having the structures of $CH_3OCF_2CFH-$ or $CF_3CFH-$ have been produced in greater amounts. Although the exact reason why the compounds presumably having the structures of $CH_3OCF_2CFH-$ or $CF_3CFH-$ are produced in greater amounts is not clarified, it is hypothesized that a methoxide ($CH_3O^-$) has a tendency to add to a vinyl group ($CF_2=CF-$) generated during the reaction.

As a process for producing a sulfonic acid group-containing monomer ($CF_2=CFO(CF_2)_2SO_3Na$) not through formation of 5-membered cyclic compounds, a process is disclosed in which $CF_3CF(COF)O(CF_2)_2SO_2F$ is subjected to a reaction with methanol to produce a methyl ester, which is neutralized with alcoholic sodium hydroxide to produce a powdered $CF_3CF(CO_2Na)O(CF_2)_2SO_3Na$, which is then decarboxylated by heating to produce $CF_2=CFO(CF_2)_2SO_3Na$. However, $CF_3CF(CO_2Na)O(CF_2)_2SO_3Na$ needs to be completely dried by eliminating alcohol and water completely prior to the decarboxylation by heating, which makes the reaction operations cumbersome (see PTL 3, for example).

[Chemical Formula 6]

$CF_3-CF-O-(CF_2)_2-SO_2F$ $\xrightarrow{CH_3OH}$
|
COF $CF_3-CF-O-(CF_2)_2-SO_2F$ $\xrightarrow{NaOH}$
|
$CO_2CH_3$ $CF_3-CF-O-(CF_2)_2-SO_3Na$ $\xrightarrow{\Delta}$
|
$CO_2Na$ $CF_2=CF-O-(CF_2)_2-SO_3Na$ Against such backgrounds, in order to produce a fluorinated monomer represented by the general formula (7) where p is 0, there has been a demand for a process capable of producing a sulfonic acid group-containing monomer serving as a synthetic intermediate of such a fluorinated monomer in a good yield and in an industrially advantageous manner.

The present disclosure is directed to provide a process capable of producing a sulfonic acid group-containing monomer in a good yield.

Solution to Problem

We have conducted extensive studies to solve the above-mentioned problems, which led to a discovery of a process capable of producing a target sulfonic acid group-containing monomer in a good yield by mixing and stirring a cyclic compound and a silanol compound, thereby completing the present disclosure.

Specifically, the present disclosure is as follows:

[1] A process for producing a sulfonic acid group-containing monomer, comprising the step of mixing and stirring the following:

a cyclic compound represented by the following general formula (1)

[Chemical Formula 7]

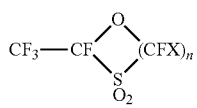

(1)

(in the formula (1), X is F or $CF_3$ and n is an integer from 1 to 6, when n is 2 or more, each CFX can be the same or different); and a silanol compound represented by the following general formula (2)

$R^1R^2R^3Si(OM)$ (2)

(in the formula (2), M is an alkali metal or an alkaline earth metal; and each of $R^1$ to $R^3$ is independently an optionally substituted hydrocarbon group having a carbon number from 1 to 10, or OM (M is an alkali metal or an alkaline earth metal), wherein the sulfonic acid group-containing monomer is represented by the following general formula (3)

$$CF_2=CFO(CFX)_nSO_3Y \quad (3)$$

(in the formula (3), n and X are the same as n and X in the general formula (1); and Y is a hydrogen atom, M, or $R^1R^2R^3Si$ (wherein M and $R^1$ to $R^3$ are the same as M and $R^1$ to $R^3$ in the general formula (2)).

[2] The process for producing a sulfonic acid group-containing monomer according to [1], wherein the method comprises the step comprising:

(i) isolating a siloxane represented by the following general formula (4) and/or a fluorine atom-containing silicon compound represented by the following general formula (5), $$R^1R^2R^3SiOSiR^1R^2R^3 \quad (4)$$

(in the formula (4), $R^1$ to $R^3$ are the same as $R^1$ to $R^3$ in the formula (2))

$$R^1R^2R^3SiF \quad (5)$$

(in the formula (5), $R^1$ to $R^3$ are the same as $R^1$ to $R^3$ in the formula (2))

from a reaction mixture containing the sulfonic acid group-containing monomer represented by the general formula (3) produced in the above step; and the siloxane represented by the general formula (4) and/or the fluorine atom-containing silicon compound represented by the general formula (5);

(ii) converting the siloxane represented by the general formula (4) and/or the fluorine atom-containing silicon compound represented by the general formula (5) isolated in (i), into the silanol compound represented by the general formula (2); and (iii) mixing and stirring the cyclic compound represented by the general formula (1) and the silanol compound represented by the general formula (2) and obtained in (ii).

[3] The process for producing a sulfonic acid group-containing monomer according to [1] or [2], wherein the silanol compound is a compound wherein M in the general formula (2) is an alkali metal.

[4] The process for producing a sulfonic acid group-containing monomer according to any one of [1] to [3], wherein the silanol compound is a compound selected from the group consisting of lithium trimethylsilanolate, lithium triethylsilanolate, lithium triisopropyl silanolate, lithium (tert-butyl)dimethyl silanolate, lithium triphenylsilanediolate, dilithium dimethyl silanediolate, dilithium diethyl silanediolate, dilithium diphenyl silanediolate, sodium trimethylsilanolate, sodium triethylsilanolate, sodium triisopropylsilanolate, sodium (tert-butyl)dimethyl silanolate, sodium triphenylsilanediolate, disodium dimethylsilanediolate, disodium diethylsilanediolate, and disodium diphenylsilanediolate.

Advantageous Effect

According to the present disclosure, a sulfonic acid group-containing monomer can be produced in a good yield.

DETAILED DESCRIPTION

Hereinafter, an embodiment for embodying the present disclosure (hereinafter simply referred to as "the present embodiment") will be described in detail.

The present disclosure is directed to a process for producing a sulfonic acid group-containing monomer, which include the step of mixing and stirring the following:

a cyclic compound represented by the following general formula (1)

[Chemical Formula 8]

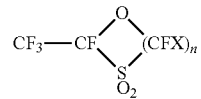

(in the formula (1), X is F or $CF_3$ and n is an integer from 1 to 6, when n is 2 or more, each CFX can be the same or different); and a silanol compound represented by the following general formula (2)

$$R^1R^2R^3Si(OM) \quad (2)$$

(in the formula (2), M is an alkali metal or an alkaline earth metal; and each of $R^1$ to $R^3$ is independently an optionally substituted hydrocarbon group having a carbon number from 1 to 10, or OM (M is an alkali metal or an alkaline earth metal), wherein the sulfonic acid group-containing monomer is represented by the following general formula (3)

$$CF_2=CFO(CFX)_nSO_3Y \quad (3)$$

(in the formula (3), n and X are the same as n and X in the above general formula (1); and Y is a hydrogen atom, M, or $R^1R^2R^3Si$ (wherein M and $R^1$ to $R^3$ are the same as M and $R^1$ to $R^3$ in the above general formula (2)).

As used herein, a cyclic compound represented by the above general formula (1), a silanol compound represented by the above general formula (2), and a sulfonic acid group-containing monomer represented by the above general formula (3) are also referred to as the "compound (1)", the "compound (2)", and "compound (3)", respectively.

Cyclic Compound (Compound (1)

In the compound (1), X is F or $CF_3$ and n is an integer from 1 to 6, and when n is 2 or more, each CFX can be the same or different. X is preferably F or $CF_3$ and n is preferably 2 to 4, in view of the availability and ease of synthesis of the compound (1).

The compound (1) can be synthesized, for example, through thermal decomposition of an alkaline metal carboxylate derived from $CF_3CF(COF)O(CFX)_nSO_2F$ (wherein X is F or $CF_3$, and n is an integer from 1 to 6) (see PTL 2, for example).

Silanol Compound (Compound (2)

In the compound (2), M is an alkali metal or an alkaline earth metal. M is preferably an alkali metal in view of the availability and ease of synthesis of the compound (2). The alkali metal is preferably lithium, sodium, or potassium, and particularly preferred are lithium and sodium in view of the reactivity with the compound (1). When a molecule of the compound (2) has more than one M, each M can be the same or different, yet M is preferably the same.

In the compound (2), $R^1$ to $R^3$ are each independently an optionally substituted hydrocarbon group having a carbon number from 1 to 10, or OM (M is an alkali metal or an alkaline earth metal). Each of $R^1$ to $R^3$ can be the same or different.

Examples of the "optionally substituted hydrocarbon group" in $R^1$ to $R^3$ include aliphatic hydrocarbon groups;

aromatic hydrocarbon groups such as a phenyl group; and fluorine-substituted hydrocarbon groups such as trifluoromethyl group in which all hydrogen atoms in a hydrocarbon group are substituted with fluorine atoms, for example.

Note that the hydrocarbon group may have a functional group if required. Examples of such a functional group include halogen atoms such as fluorine atom, chlorine atom, and bromine atom, a nitrile group (—CN), ether group (—O—), carbonate group (—OCO$_2$—), ester group (—CO$_2$—), carbonyl group (—CO—), sulfide group (—S—), sulfoxide group (—SO—), sulfonyl group (—SO$_2$—), and urethane group (—NHCO$_2$—).

The carbon number in each hydrocarbon group in each of $R^1$ to $R^3$ is from 1 to 10, more preferably from 1 to 8 in view of the availability of the compound (2), and particularly preferably from 1 to 6 in view of the reactivity with the compound (1).

Examples of $R^1$ to $R^3$ include aliphatic hydrocarbon groups such as methyl group, ethyl group, vinyl group, allyl group, 1-methylvinyl group, n-propyl group, isopropyl group, n-butyl group, isobutyl group, sec-butyl group, tent-butyl group, and fluoromethyl group; and aromatic hydrocarbon group such as benzyl group, phenyl group, nitrile-substituted phenyl group, and fluorinated phenyl group. Of these, methyl group, ethyl group, n-propyl group, isopropyl group, n-butyl group, isobutyl group, sec-butyl group, tent-butyl group, benzyl group, and phenyl group are more preferable, and methyl group, ethyl group, isopropyl group, tent-butyl group, and phenyl group are particularly preferable.

Examples of the compound (2) include lithium trimethylsilanolate, lithium triethyl silanolate, lithium triisopropyl silanolate, lithium (tert-butyl)dimethyl silanolate, lithium triphenylsilanediolate, dilithium dimethylsilanediolate, dilithium diethyl silanediolate, dilithium diphenylsilanediolate, sodium trimethylsilanolate, sodium triethylsilanolate, sodium triisopropylsilanolate, sodium (tert-butyl)dimethyl silanolate, sodium triphenylsilanediolate, disodium dimethylsilanediolate, disodium diethylsilanediolate, and disodium diphenylsilanediolate.

The compound (2) may be a commercially-available product, or may be synthesized from an available compound, such as a halogenated silane, a silanol, and a siloxane, for example.

A process for synthesizing the compound (2) is as follows. A halogenated silane ($R^1R^2R^3SiZ$) (wherein $R^1$ to $R^3$ are as defined in the compound (2); Z represents a fluorine atom, a chlorine atom, a bromine atom, or an iodine atom, and when Z is a fluorine atom, it corresponds to the compound (5)) is hydrolyzed to be converted into a silanol ($R^1R^2R^3SiOH$) (wherein $R^1$ to $R^3$ are as defined in the compound (2)) or a siloxane ($R^1R^2R^3SiOSiR^1R^2R^3$) (wherein $R^1$ to $R^3$ are as defined in the compound (2)), for example. Subsequently, the silanol is subjected to a reaction with M, MH, RM, or the like (M is as defined in the compound (2), and R represents an alkyl or aryl group having a carbon number from 1 to 10), or the siloxane is subjected to a reaction with MOH, M$_2$O, MNH$_2$, RM, or the like (M is as defined in the compound (2), and R represents an alkyl or aryl group having a carbon number from 1 to 10), to thereby synthesize the compound (2).

Examples of M used for the reaction with the silanol include Li, Na, and K. Examples of MH include LiH, NaH, and KH. Examples of RM include n-C$_4$H$_9$Li, sec-C$_4$H$_9$Li, tert-C$_4$H$_9$Li, CH$_3$Li, C$_6$H$_5$Li, n-C$_4$H$_9$Na, and n-C$_4$H$_9$K. Of these, MH and RM are preferred in view of the reactivity with the silanol and controllability of the reaction in an industrial scale, and more preferred are NaH, KH, n-C$_4$H$_9$Li, and CH$_3$Li.

The amount of above-mentioned M, MH, or RM used is preferably from 0.95 mol to 2 mol relative to 1 mol of hydroxyl groups in the silanol. The reaction temperature is preferably from −100° C. to 200° C., and the reaction time is preferably from 0.01 hours to 100 hours.

Examples of MOH used for the reaction with the siloxane include LiOH, NaOH, and KOH. Examples of M$_2$O include Li$_2$O, Na$_2$O, and K$_2$O. Examples of MNH$_2$ include LiNH$_2$, NaNH$_2$, and KNH$_2$. Examples of RM include n-C$_4$H$_9$Li, sec-C$_4$H$_9$Li, tert-C$_4$H$_9$Li, CH$_3$Li, C$_6$H$_5$Li, n-C$_4$H$_9$Na, and n-C$_4$H$_9$K. Of these, MOH and RM are preferred in view of the reactivity with the siloxane and controllability of the reaction in an industrial scale, and more preferred are NaOH, KOH, n-C$_4$H$_9$Li, and CH$_3$Li.

The amount of the above-mentioned MOH, M$_2$O, MNH$_2$, and RM used is preferably from 0.95 mol to 4 mol relative to 1 mol of siloxane bonds (Si—O—Si) in the siloxane. The reaction temperature is preferably from −100° C. to 200° C., and the reaction time is preferably from 0.01 hours to 100 hours. When MOH is used, water may be generated in the reaction system. In order to remove the generated water, LiH, NaH, KH, MgO, CaO, CaCl$_2$, MgSO$_4$, Na$_2$SO$_4$, molecular sieves, or active alumina may be added in the reaction system as a dehydrating agent, for example. The amount of LiH, NaH, KH, MgO, CaO, CaCl$_2$, MgSO$_4$, or Na$_2$SO$_4$ used is preferably 0.95 mol to 4 mol relative to 1 mol of siloxane bonds (Si—O—Si) in the siloxane. The amount of the molecular sieves or active alumina used is preferably from 1 g to 180 g relative to 1 mol of siloxane bonds (Si—O—Si) in the siloxane.

[Chemical Formula 9]

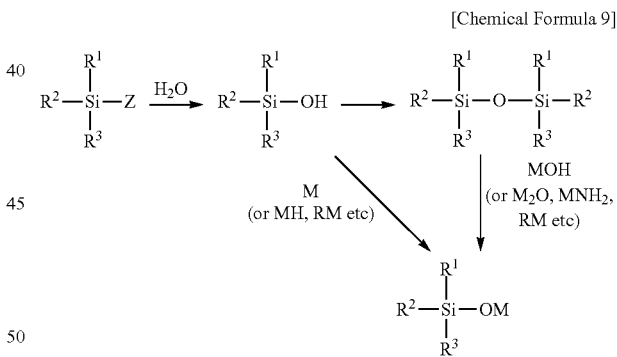

Production of Sulfonic Acid Group-Containing Monomer (Compound (3))

The compound (3) can be produced by mixing and stirring the compound (1) and the compound (2).

The exact reason why the compound (3) is produced in a good yield by mixing and stirring the compound (1) and the compound (2) has not been clarified. It is hypothesized as indicated below that the compound (1) is ring-opened by the compound (2) to form a sulfonic acid silyl ester (CF$_2$=CFO (CFX)$_n$SO$_3$SiR$^1$R$^2$R$^3$), of which O—Si bond is then cleaved by the compound (2) and/or a metal fluoride (MF) to yield the compound (3).

[Chemical Formula 10]

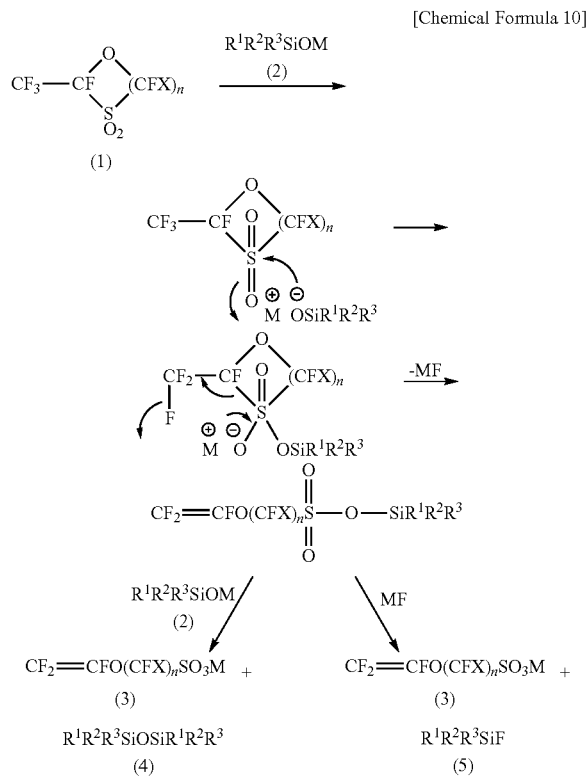

As described above, when a 5-membered cyclic compound is subjected to a reaction with sodium methoxide (NaOCH$_3$), for example, in place of the compound (2), a complex reaction mixture is produced in which the amount of production of the target sulfonic acid group-containing monomer (CF$_2$═CFO(CF$_2$)$_2$SO$_3$Na) is small, but compounds presumably having the structures of CH$_3$OCF$_2$CFH— or CF$_3$CFH— have been produced in greater amounts. Alternatively, when a 5-membered cyclic compound is reacted with potassium tert-butoxide (KOtC$_4$H$_9$), which is known to be a bulky base, instead of the compound (2), a complex reaction mixture is similarly produced in which the amount of production of the target sulfonic acid group-containing monomer (CF$_2$═CFO (CF$_2$)$_2$SO$_3$K) is small, but compounds presumably having the structures of tC$_4$H$_9$OCF$_2$CFH— or CF$_3$CFH— have been produced in greater amounts.

From these facts, as the reason why the compound (1) and the compound (2) give the compound (3) in a good yield, it is hypothesized the compound (2) is a silicon compound and has a bulky structure and hence is difficult to add to the vinyl group site in the generated compound (3).

In the production process of the present embodiment, a solvent is preferably used during the mixing and stirring.

A wide variety of aprotic polar solvents can be used as long as they are inert during reaction, and examples of aprotic polar solvents include ether group-containing solvents, such as tetrahydrofuran, 1,2-dimethoxyethane, 1,2-diethoxyethane, 1,4-dioxane, cyclopentyl methyl ether, ethylene glycol dimethyl ether, diethylene glycol dimethyl ether, triethylene glycol dimethyl ether, tetraethylene glycol dimethyl ether, and 4-methyltetrahydropyran; nitrile group-containing solvents such as acetonitrile; and sulfonyl group-containing solvents such as sulfolane. Of these, an ether group-containing solvent such as tetrahydrofuran, 1,2-dimethoxyethane, 1,2-diethoxyethane, and 4-methyl tetrahydropyran is preferably used for producing the compound (3) in a good yield.

In the production process of the present embodiment, the compound (2) is used preferably in an amount of the molar equivalent or more of the compound (1), more preferably in an amount of 1 to 4 times molar equivalent of the compound (1), and most preferably in an amount of 1 to 3 times molar equivalent of the compound (1).

The temperature of the mixing and stirring is preferably −80° C. to 100° C., and more preferably −50° C. to 80° C.

The time of mixing and stirring is preferably 0.01 to 50 hours, and more preferably 0.1 to 10 hours.

The production process of the present embodiment may give, together with the target compound (3), a proton adduct represented by the following general formula (8) (hereinafter referred to as the "compound (8)") as a by-product:

$$CF_3CFHO(CFX)_nSO_3Y \qquad (8)$$

(in the formula (8), n and X are the same as n and X in the above general formula (1), Y is a hydrogen atom, M, or R$^1$R$^2$R$^3$Si (M and R$^1$ to R$^3$ are the same as M and R$^1$ to R$^3$ in the above general formula (2)). The compound (8) is known to be readily converted into the compound (3) through addition of a bulky base such as lithium hexamethyl disilazide to the compound (8), as disclosed in NPL 2.

Other than the above-described compound (8), the production process of the present embodiment gives a siloxane represented by the following general formula (4) (hereinafter referred to as the "compound (4)")

$$R^1R^2R^3SiOSiR^1R^2R^3 \qquad (4)$$

(in the formula (4), R$^1$ to R$^3$ are the same as R$^1$ to R$^3$ in the above formula (2)); and/or a fluorine atom-containing silicon compound represented by the following general formula (5) (hereinafter referred to as the "compound (5)")

$$R^1R^2R^3SiF \qquad (5)$$

(in the formula (5), R$^1$ to R$^3$ are the same as R$^1$ to R$^3$ in the above general formula (2)) as by-products, together with the target compound (3).

Further, the reaction may also give a metal fluoride (MF) (M is as defined in the above general formula (2)) which may be present in the reaction system. Although the exact reason why the compound (4), the compound (5), and the metal fluoride (MF) are produced as the by-products is not clarified, it is hypothesized that the by-products are generated by the mechanism described above.

We have also conducted extensive studies on a production process of the present embodiment which includes (i) isolating the compound (4) and/or the compound (5) from a reaction mixture containing the target compound (3) and the compound (4) and/or the compound (5) as the by-products, which are produced by mixing and stirring the compound (1) and the compound (2); followed by (ii) converting the isolated compound (4) and/or compound (5) into the compound (2); and (iii) mixing and stirring the compound (1) and the compound (2) obtained in (ii), to thereby produce the compound (3). We have found this process industrially advantageous, which will be described below.

A wide variety of isolation techniques can be employed to isolate the respective components from the reaction mixture containing the target compound (3) and the compound (4) and/or the compound (5) as by-products. Exemplary techniques include isolation by distillation, and isolation by extraction by means of an organic solvent or water. When a metal fluoride (MF) is precipitated or suspended in a suspension, the metal fluoride may be removed by filtration before isolation and purification.

For example, in isolation by distillation, the compound (3) can be isolated by distilling off a solvent used and the compound (4) and/or the compound (5) from the solution or suspension subsequent to the reaction. The distillate containing the solvent, and the compound (4) and/or the compound (5) that have been distilled off may be subjected to further distillation or extraction to separate the solvent, and the compound (4) and/or the compound (5) from each other.

In isolation by extraction by means of an organic solvent or water, for example, a solvent used is distilled off from the solution or suspension subsequent to the reaction. Water is then added to the residue to thereby cause the compound (3) to be dissolved into the water, so that the compound (3) can be isolated by filtration or the like.

The compound (4) and/or the compound (5) obtained through the above isolation can be readily converted into the compound (2), which is then mixed and stirred with the compound (1) for production of the compound (3), as described above regarding the synthesis of the silanol compound (compound (2)).

As described above, the present disclosure enables an efficient production of a sulfonic acid group-containing monomer which serves as a raw material of various fluorine-based polymer electrolytes having high heat resistances, such as membranes for fuel cells, catalyst binder polymers for fuel cells, and membranes for chlor-alkali electrolysis.

EXAMPLES

While the present disclosure will now be described in more details with reference to examples and comparative examples, it is understood that the present disclosure is not limited to these examples.

The analytical techniques used in examples and comparative examples are as follows:

Nuclear magnetic resonance spectrometry (NMR): molecular structure analyses by $^1$H-NMR and $^{19}$F-NMR
Analytical apparatus: nuclear magnetic resonance apparatus type JNM-ECZ400S (manufactured by JEOL Ltd.)
Solvents: deuterochloroform and deuterium oxide
Reference material: $CFCl_3$ (0 ppm)

Example 1

A 3-L round-bottomed flask equipped with a mechanical stirrer, a dropping funnel, and a reflux condenser was charged with sodium carbonate (328.6 g, 3.10 mol) which had been dried at 180° C. for 6 hours, and tetraglyme (1000 mL). While the temperature inside the reactor was kept 30° C. or lower, $CF_3CF(COF)OCF_2CF_2SO_2F$ (934.2 g, 2.70 mol) was added dropwise for more than 3 hours. After the dropwise addition completed, the reaction mixture was further stirred at 40° C. for 1 hour to yield a carboxylic acid sodium salt ($CF_3CF(CO_2Na)OCF_2CF_2SO_2F$). The resultant reaction mixture was heated at 160° C. under normal pressure to induce decarboxylation. A volatile component was distilled off, which was collected in an ice-cooled vessel. This colorless liquid was identified as the cyclic compound (741.9 g, 2.65 mol; yield: 98%) by $^{19}$F-NMR.

[Chemical Formula 11]

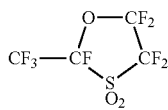

$^{19}$F-NMR: δ (ppm) −124.7 (1F), −120.6 (1F), −115.4 (1F), −90.1 (1F), −80.5 (3F), −78.0 (1F)

A 500-mL 4-necked flask under a nitrogen atmosphere was charged with the cyclic compound (20.39 g, 73 mmol) produced in the above-mentioned step, and was cooled to 0° C. Next, a solution of sodium trimethylsilanolate (available from Sigma Aldrich Co., LLC; 16.03 g, 143 mmol) dissolved in 4-methyltetrahydropyran (120.85 g) was added dropwise to this flask for 1 hour, followed by further stirring at room temperature for 2 hours. The resultant reaction mixture was sampled, of which analysis by $^{19}$F-NMR indicated disappearance of the cyclic compound and production of 93% by mol of $CF_2$=$CFOCF_2CF_2SO_3Na$ and 7% by mol of $CF_3CFHOCF_2CF_2SO_3Na$. Formation of trimethylsilyl fluoride (boiling point: 16° C.) was confirmed at −158.5 ppm by $^{19}$F-NMR, and formation of hexamethyldisiloxane (boiling point: 100° C.) was confirmed at 0.8 ppm by $^1$H-NMR. The resultant reaction mixture was heated under reduced pressure (190 hPa), and a liquid (125.22 g) was distilled off and a solid residue (28.7 g) remained. The distilled liquid was identified to be a mixture of 4-methyltetrahydropyran (91.0% by mass) and hexamethyldisiloxane (9.0% by mass) by $^1$H-NMR (internal standard: benzotrifluoride). In addition, the solid residue was identified to contain 70.0% by mass (yield: 92%) of $CF_2$=$CFOCF_2CF_2SO_3Na$ and 6.4% by mass (yield: 8%) of $CF_3CFHOCF_2CF_2SO_3Na$ by $^{19}$F-NMR (internal standard: trifluoroethanol).

$CF_2$=$CFOCF_2CF_2SO_3Na$ $^{19}$F-NMR: δ (ppm) −136.3 (1F), −123.3 (1F), −118.8 (2F), −115.4 (1F), −85.4 (2F)

$CF_3CFHOCF_2CF_2SO_3Na$ $^{19}$F-NMR: δ (ppm) −147.3 (1F), −118.8 (2F), −85.8 (1F), −85.0 (3F), −84.3 (1F)

Example 2

A 50-mL 4-necked flask under a nitrogen atmosphere was charged with hexamethyldisiloxane (1 g, 6 mmol), which had been obtained by purification by distillation from the distillate liquid (the mixture of 4-methyltetrahydropyran and hexamethyldisiloxane) prepared as described in Example 1, sodium hydroxide (0.49 g, 12 mmol), NaH (content: 62%) (0.70 g, 18 mmol), and 1,2-dimethoxyethane (4 g). The system was heated at 85° C. for 10 hours, and was then cooled to room temperature. Insoluble components were filtered out to prepare a solution of sodium trimethylsilanolate in 1,2-dimethoxyethane.

A 50-mL 4-necked flask under a nitrogen atmosphere was charged with the cyclic compound (1.71 g, 6 mmol) prepared as described in Example 1. The solution of sodium trimethylsilanolate in 1,2-dimethoxyethane as prepared above was added dropwise while the system was cooled to 0° C., followed by further stirring at room temperature for 1 hour. The resultant reaction mixture was sampled, of which analysis by $^{19}$F-NMR indicated disappearance of the cyclic compound and production of 87% by mol of $CF_2$=$CFOCF_2CF_2SO_3Na$ and 13% by mol of $CF_3CFHOCF_2CF_2SO_3Na$. Further, formation of trimethylsilyl fluoride was confirmed at −158.5 ppm.

Example 3

A 50-mL 2-neck flask under a nitrogen atmosphere was charged with NaH (content: 62%) (0.308 g, 8.0 mmol) and 1,2-dimethoxyethane (3 g), and was cooled to 0° C. To this flask, a solution of triphenylsilanol (available from Tokyo Chemical Industry Co., Ltd.; 1.972 g, 7.1 mmol) dissolved in 1,2-dimethoxyethane (3 g) was added dropwise, followed by further stirring at 0° C. for 30 minutes, thereby preparing a solution of sodium triphenylsilanolate in 1,2-dimethoxyethane.

A 50-mL 2-necked flask under a nitrogen atmosphere was charged with the cyclic compound (1.00 g, 3.6 mmol) prepared as described in Example 1, and was cooled to 0° C. The solution of sodium triphenylsilanolate in 1,2-dimethoxyethane prepared as described above was added dropwise to the flask, followed by further stirring at 0° C. for 1 hour. The resultant reaction mixture was sampled, of which analysis by $^{19}$F-NMR indicated disappearance of the cyclic compound and production of 95% by mol of $CF_2$=$CFOCF_2CF_2SO_3Na$ and 5% by mol of $CF_3CFHOCF_2CF_2SO_3Na$. Further, formation of triphenylsilyl fluoride was confirmed at −170.1 ppm.

Example 4

A 200-mL 3-necked flask under a nitrogen atmosphere is charged with a solution of 1 M of sodium trimethylsilanolate in tetrahydrofuran (available from Sigma Aldrich Co., LLC; 44 mL, 44 mmol), and the cyclic compound (5.60 g, 20 mmol) prepared as described in Example 1 was added dropwise while the system was ice-cooled, followed by stirring at room temperature for 2 hours. Distillation of the liquid from the resultant reaction mixture under reduced pressure gave a yellow solid (9.64 g). The resultant yellow solid was identified to contain 57% by mass (yield: 93%) of $CF_2$=$CFOCF_2CF_2SO_3Na$ and 4.7% by mass (yield: 7%) of $CF_3CFHOCF_2CF_2SO_3Na$ from $^{19}$F-NMR (internal standard: hexafluorobenzene).

Example 5

The same procedure as in Example 3 was carried out except that triethylsilanol (available from Tokyo Chemical Industry Co., Ltd.) was used instead of triphenylsilanol used in Example 3. The resultant reaction mixture was sampled, of which analysis by $^{19}$F-NMR indicated disappearance of the cyclic compound and production of 83% by mol of $CF_2$=$CFOCF_2CF_2SO_3Na$ and 17% by mol of $CF_3CFHOCF_2CF_2SO_3Na$. Further, formation of triethylsilyl fluoride was confirmed at −176.1 ppm.

Example 6

A 100-mL 3-necked flask under a nitrogen atmosphere was charged with lithium trimethylsilanolate (available from Sigma Aldrich Co., LLC; 2.11 g, 22 mmol) and 1,2-dimethoxyethane (30 mL), which were stirred. The cyclic compound (5.60 g, 20 mmol) prepared as described in Example 1 was then added dropwise while the system was ice-cooled, followed by further stirring at room temperature for 2 hours. The resultant reaction mixture was sampled, of which analysis by $^{19}$F-NMR indicated disappearance of the cyclic compound and production of 90% by mol of $CF_2$=$CFOCF_2CF_2SO_3Li$ and 10% by mol of $CF_3CFHOCF_2CF_2SO_3Li$. Further, formation of trimethylsilyl fluoride was confirmed at −158.5 ppm. Distillation of the liquid from the resultant reaction mixture under reduced pressure gave a yellow solid (7.60 g). The resultant yellow solid was identified to contain 67% by mass (yield: 90%) of $CF_2$=$CFOCF_2CF_2SO_3Li$ and 8% by mass (yield: 10%) of $CF_3CFHOCF_2CF_2SO_3Li$ from $^{19}$F-NMR (internal standard: hexafluorobenzene).

Example 7

A 100-mL 3-necked flask under a nitrogen atmosphere was charged with triethylsilanol (available from Tokyo Chemical Industry Co., Ltd.; 0.66 g, 5 mmol), and tetrahydrofuran (12 mL), which was cooled to 0° C. A solution of 1.6M of n-butyl lithium in hexane (3.1 mL) was then added dropwise, followed by further stirring at 0° C. for 30 minutes, thereby preparing a solution of lithium triethylsilanolate in tetrahydrofuran. The cyclic compound (1.40 g, 5 mmol) prepared as described in Example 1 was added dropwise to this flask, followed by stirring at 0° C. for 30 minutes and further stirring at room temperature for 2 hours. The resultant reaction mixture was sampled, of which analysis by $^{19}$F-NMR indicated disappearance of the cyclic compound and production of 82% by mol of $CF_2$=$CFOCF_2CF_2SO_3Li$ and 18% by mol of $CF_3CFHOCF_2CF_2SO_3Li$. Further, formation of triethylsilyl fluoride was confirmed at −176.8 ppm.

Example 8

The same procedure as in Example 7 was carried out except that triphenylsilanol (available from Tokyo Chemical Industry Co., Ltd.) was used instead of triethylsilanol used in Example 7. The resultant reaction mixture was sampled, of which analysis by $^{19}$F-NMR indicated disappearance of the cyclic compound and production of 80% by mol of $CF_2$=$CFOCF_2CF_2SO_3Li$ and 20% by mol of $CF_3CFHOCF_2CF_2SO_3Li$. Further, formation of triphenylsilyl fluoride was confirmed at −170.9 ppm.

Comparative Example 1

A 50-mL 3-necked flask under a nitrogen atmosphere was charged with sodium methoxide ($NaOCH_3$) (0.19 g, 3.52 mmol) and diethyl ether (7 mL), followed by stirring. The cyclic compound (1.19 g, 4.25 mmol) prepared as described in Example 1 was then added dropwise while the system was ice-cooled, followed by further stirring at room temperature for 24 hours. An analysis by $^{19}$F-NMR indicated that the cyclic compound (37% by mol) remained, and the target compound $CF_2$=$CFOCF_2CF_2SO_3Na$ (13% by mol) and compounds (50% by mol) presumably having the structures of $CH_3OCF_2CFH$— or $CF_3CFH$— were produced, in the resultant reaction mixture.

Comparative Example 2

A 50-mL 3-necked flask under a nitrogen atmosphere was charged with potassium tert-butoxide ($KOtC_4H_9$) (1.12 g, 10 mmol) and 1,2-dimethoxyethane (10 mL), followed by stirring. The cyclic compound (2.80 g, 10 mmol) prepared as described in Example 1 was then added dropwise while the system was ice-cooled, followed by further stirring at room temperature for 24 hours. An analysis by $^{19}$F-NMR indicated that the cyclic compound (33% by mol) remained, and the target compound $CF_2$=$CFOCF_2CF_2SO_3K$ (15% by mol) and compounds (52% by mol) presumably having the structures of $tC_4H_9OCF_2CFH$— or $CF_3CFH$— were produced, in the resultant reaction mixture.

INDUSTRIAL APPLICABILITY

According to the present disclosure, a sulfonic acid group-containing monomer can be produced in a good yield, which is a raw material of fluorine-based polymer electrolytes having high heat resistances useful for applications, such as membranes for fuel cells, catalyst binder polymers for fuel cells, and membranes for chlor-alkali electrolysis.

The invention claimed is:

1. A process for producing a sulfonic acid group-containing monomer, comprising the step of mixing and stirring the following:

a cyclic compound represented by the following general formula (1)

[Chemical Formula 1]

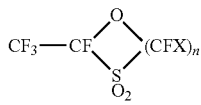
(1)

(in the formula (1), X is F or $CF_3$ and n is an integer from 1 to 6, when n is 2 or more, each CFX can be the same or different); and a silanol compound represented by the following general formula (2)

$$R^1R^2R^3Si(OM) \quad (2)$$

(in the formula (2), M is an alkali metal or an alkaline earth metal; and each of $R^1$ to $R^3$ is independently an optionally substituted hydrocarbon group having a carbon number from 1 to 10, or OM (M is an alkali metal or an alkaline earth metal), wherein the sulfonic acid group-containing monomer is represented by the following general formula (3)

$$CF_2=CFO(CFX)_nSO_3Y \quad (3)$$

(in the formula (3), n and X are the same as n and X in the general formula (1); and Y is a hydrogen atom, M, or $R^1R^2R^3Si$ (wherein M and $R^1$ to $R^3$ are the same as M and $R^1$ to $R^3$ in the general formula (2)).

2. The process for producing a sulfonic acid group-containing monomer according to claim 1, wherein the method comprises the step comprising:

(i) isolating a siloxane represented by the following general formula (4) and/or a fluorine atom-containing silicon compound represented by the following general formula (5), $$R^1R^2R^3SiOSiR^1R^2R^3 \quad (4)$$

(in the formula (4), $R^1$ to $R^3$ are the same as $R^1$ to $R^3$ in the formula (2))

$$R^1R^2R^3SiF \quad (5)$$

(in the formula (5), $R^1$ to $R^3$ are the same as R1 to $R^3$ in the formula (2))

from a reaction mixture containing the sulfonic acid group-containing monomer represented by the general formula (3) produced in the above step; and the siloxane represented by the general formula (4) and/or the fluorine atom-containing silicon compound represented by the general formula (5);

(ii) converting the siloxane represented by the general formula (4) and/or the fluorine atom-containing silicon compound represented by the general formula (5) isolated in (i), into the silanol compound represented by the general formula (2); and (iii) mixing and stirring the cyclic compound represented by the general formula (1) and the silanol compound represented by the general formula (2) and obtained in (ii).

3. The process for producing a sulfonic acid group-containing monomer according to claim 1, wherein the silanol compound is a compound wherein M in the general formula (2) is an alkali metal.

4. The process for producing a sulfonic acid group-containing monomer according to claim 1, wherein the silanol compound is a compound selected from the group consisting of lithium trimethylsilanolate, lithium triethylsilanolate, lithium triisopropylsilanolate, lithium (tert-butyl) dimethylsilanolate, lithium triphenylsilanediolate, dilithium dimethylsilanediolate, dilithium diethylsilanediolate, dilithium diphenylsilanediolate, sodium trimethylsilanolate, sodium triethylsilanolate, sodium triisopropylsilanolate, sodium (tert-butyl)dimethylsilanolate, sodium triphenylsilanediolate, disodium dimethylsilanediolate, disodium diethylsilanediolate, and disodium diphenylsilanediolate.

5. The process for producing a sulfonic acid group-containing monomer according to claim 2, wherein the silanol compound is a compound wherein M in the general formula (2) is an alkali metal.

6. The process for producing a sulfonic acid group-containing monomer according to claim 2, wherein the silanol compound is a compound selected from the group consisting of lithium trimethylsilanolate, lithium triethylsilanolate, lithium triisopropylsilanolate, lithium (tert-butyl) dimethylsilanolate, lithium triphenylsilanediolate, dilithium dimethylsilanediolate, dilithium diethylsilanediolate, dilithium diphenylsilanediolate, sodium trimethylsilanolate, sodium triethylsilanolate, sodium triisopropylsilanolate, sodium (tert-butyl)dimethylsilanolate, sodium triphenylsilanediolate, disodium dimethylsilanediolate, disodium diethylsilanediolate, and disodium diphenylsilanediolate.

7. The process for producing a sulfonic acid group-containing monomer according to claim 3, wherein the silanol compound is a compound selected from the group consisting of lithium trimethylsilanolate, lithium triethylsilanolate, lithium triisopropylsilanolate, lithium (tert-butyl) dimethylsilanolate, lithium triphenylsilanediolate, dilithium dimethylsilanediolate, dilithium diethylsilanediolate, dilithium diphenylsilanediolate, sodium trimethylsilanolate, sodium triethylsilanolate, sodium triisopropylsilanolate, sodium (tert-butyl)dimethylsilanolate, sodium triphenylsilanediolate, disodium dimethylsilanediolate, disodium diethylsilanediolate, and disodium diphenylsilanediolate.

* * * * *